(12) United States Patent
Kanayama

(10) Patent No.: US 10,772,608 B2
(45) Date of Patent: Sep. 15, 2020

(54) MEDICAL IMAGE DIAGNOSTIC APPARATUS AND MEDICAL INFORMATION DISPLAY CONTROL METHOD

(71) Applicant: Toshiba Medical Systems Corporation, Otawara-shi (JP)

(72) Inventor: Yuko Kanayama, Kawasaki (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1042 days.

(21) Appl. No.: 15/200,630

(22) Filed: Jul. 1, 2016

(65) Prior Publication Data

US 2017/0086795 A1    Mar. 30, 2017

(30) Foreign Application Priority Data

Sep. 30, 2015    (JP) .................................. 2015-195068

(51) Int. Cl.
*A61B 8/08*    (2006.01)
*A61B 8/00*    (2006.01)
*A61B 8/06*    (2006.01)

(52) U.S. Cl.
CPC .............. *A61B 8/485* (2013.01); *A61B 8/469* (2013.01); *A61B 8/5207* (2013.01); *A61B 8/5223* (2013.01); *A61B 8/06* (2013.01); *A61B 8/0883* (2013.01); *A61B 8/4444* (2013.01); *A61B 8/4483* (2013.01); *A61B 8/461* (2013.01); *A61B 8/488* (2013.01); *A61B 8/54* (2013.01)

(58) Field of Classification Search
CPC ....... A61B 8/485; A61B 8/469; A61B 8/5207; A61B 8/5223
See application file for complete search history.

(56) References Cited

U.S. PATENT DOCUMENTS

| | | | |
|---|---|---|---|
| 8,469,891 B2 * | 6/2013 | Maleke .................. | A61B 5/055 600/438 |
| 8,532,430 B2 * | 9/2013 | Hazard .................. | A61B 8/485 382/103 |
| 8,545,407 B2 * | 10/2013 | Bercoff .................... | A61B 8/08 600/438 |
| 9,072,493 B1 * | 7/2015 | Yoshikawa ............ | A61B 8/485 |
| 9,173,634 B2 * | 11/2015 | Matsunaka .......... | A61B 8/0858 |
| 9,244,041 B2 * | 1/2016 | Gallippi ................. | A61B 8/485 |
| 9,554,777 B2 * | 1/2017 | Kim .................... | G01N 29/0654 |

(Continued)

FOREIGN PATENT DOCUMENTS

| | | |
|---|---|---|
| JP | 6-292670 A | 10/1994 |
| JP | 2005-168542 A | 6/2005 |

(Continued)

OTHER PUBLICATIONS

Japanese Office Action dated May 23, 2019 in Japanese Patent Application No. 2015-195068, 3 pages.

*Primary Examiner* — Anand P Bhatnagar
(74) *Attorney, Agent, or Firm* — Oblon, McClelland, Maier & Neustadt, L.L.P.

(57) ABSTRACT

A medical image diagnostic apparatus of embodiments includes processing circuitry configured to: calculate an index value in a region of interest of a subject based on tissue property data collected by scanning on the subject; and determine display characteristics of the region of interest based on the index value.

22 Claims, 11 Drawing Sheets

(56) References Cited

U.S. PATENT DOCUMENTS

| | | | |
|---|---|---|---|
| 9,801,615 B2* | 10/2017 | Salcudean | A61B 8/485 |
| 2009/0299179 A1* | 12/2009 | Main | A61B 8/065 |
| | | | 600/438 |
| 2010/0094133 A1 | 4/2010 | Yoshiara et al. | |
| 2014/0094702 A1* | 4/2014 | Kim | G01N 29/0654 |
| | | | 600/438 |

FOREIGN PATENT DOCUMENTS

| | | |
|---|---|---|
| JP | 2006-26079 A | 2/2006 |
| JP | 2009-95512 A | 5/2009 |
| JP | 2010-22565 A | 2/2010 |
| JP | 2010-94220 | 4/2010 |
| JP | 2011-224143 A | 11/2011 |
| JP | 2013-111434 A | 6/2013 |
| JP | 5473527 | 4/2014 |
| JP | 5623609 | 11/2014 |

* cited by examiner

FIG.2
| TYPE OF INDEX VALUE | THRESHOLD |
|---|---|
| AVERAGE VALUE OF SHEAR WAVE VELOCITIES | 2.0 |
| STANDARD DEVIATION OF SHEAR WAVE VELOCITIES | 1.0 |
| ⋮ | ⋮ |
FIG.3A
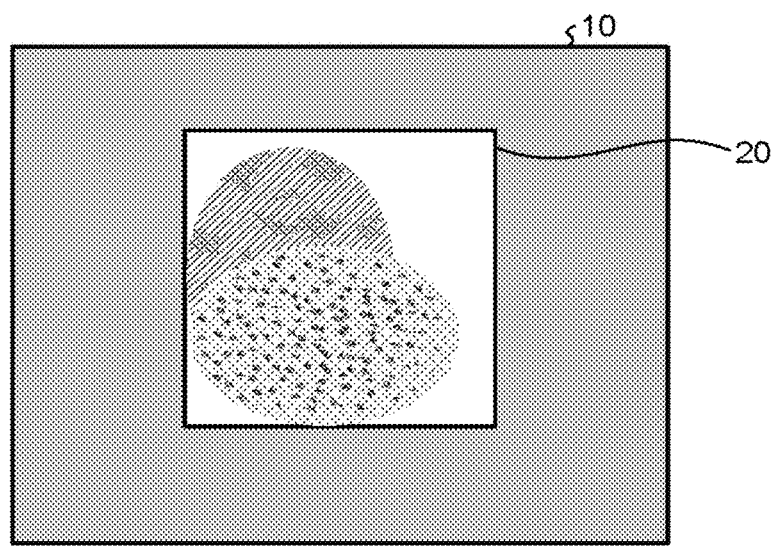
FIG.3B
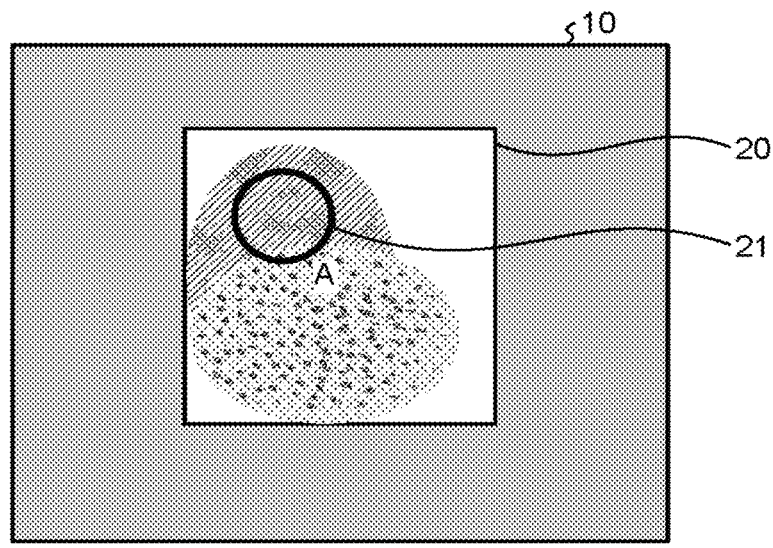

FIG.5A

| RANK ORDER | ROI INFORMATION | SWS [m/s] | SD [m/s] |
|---|---|---|---|
| 1 | A | 1.84 | 1.01 |

FIG.5B

| RANK ORDER | ROI INFORMATION | SWS [m/s] | SD [m/s] |
|---|---|---|---|
| 1 | C | 1.52 | 0.23 |
| 2 | A | 1.84 | 1.01 |
| 3 | B | 2.09 | 1.35 |

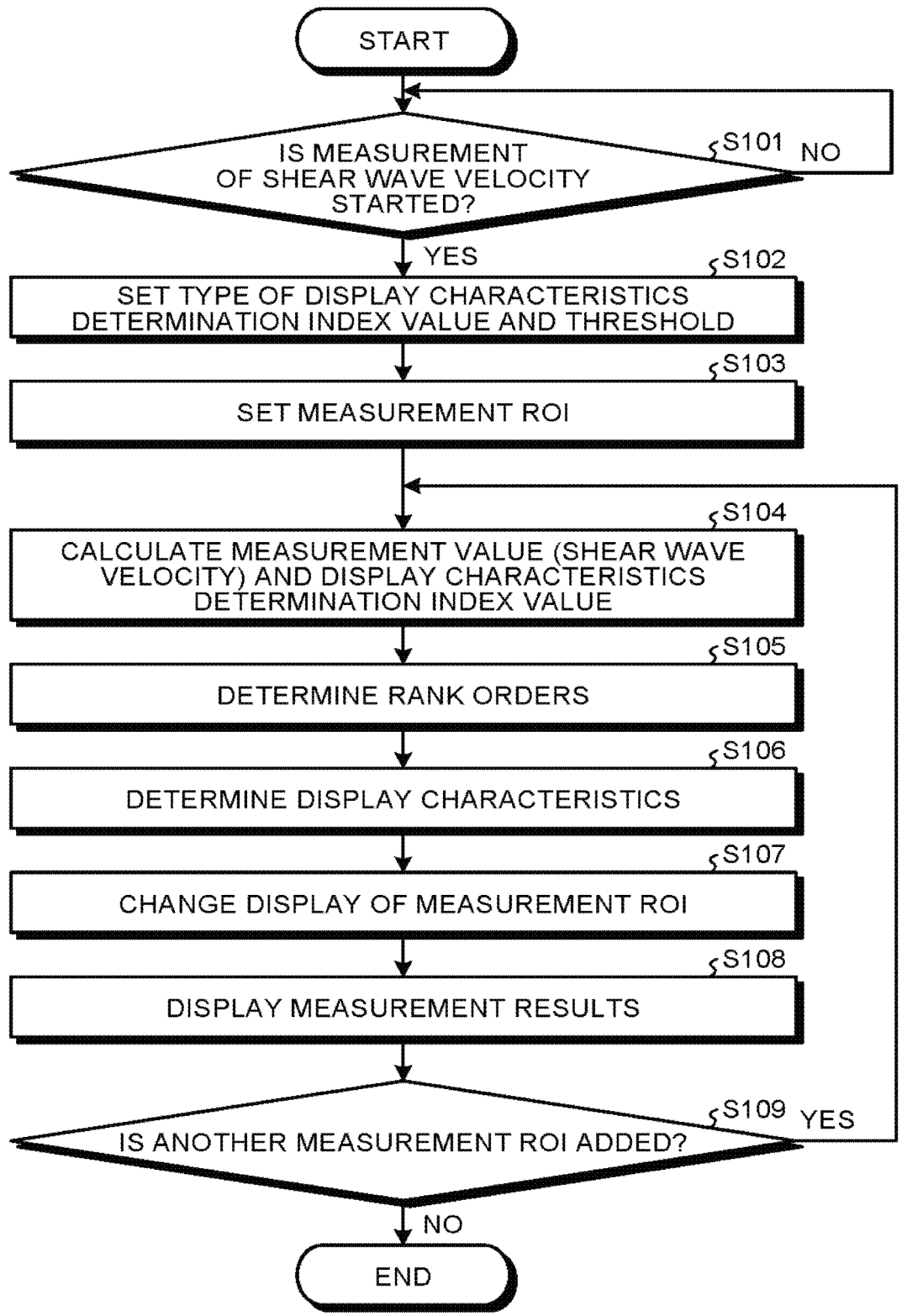

FIG.7

| TYPE OF INDEX VALUE | THRESHOLD |
|---|---|
| AVERAGE VALUE OF SHEAR WAVE VELOCITIES | 1.4, 1.6, 1.8, 2.0 |
| STANDARD DEVIATION OF SHEAR WAVE VELOCITIES | 1.0 |

FIG.8

| RANGE OF AVERAGE VALUE OF SHEAR WAVE VELOCITIES | DISPLAY COLOR |
|---|---|
| 2.0 TO | BLACK |
| 1.8 TO 2.0 | RED |
| 1.6 TO 1.8 | ORANGE |
| 1.4 TO 1.6 | YELLOW |
| TO 1.4 | WHITE |

FIG.9

| RANGE OF STANDARD DEVIATION OF SHEAR WAVE VELOCITIES | LINE TYPE |
|---|---|
| 1.0 TO | DOTTED LINE |
| TO 1.0 | SOLID LINE |

MEDICAL IMAGE DIAGNOSTIC APPARATUS AND MEDICAL INFORMATION DISPLAY CONTROL METHOD

CROSS-REFERENCE TO RELATED APPLICATIONS

This application is based upon and claims the benefit of priority from Japanese Patent Application No. 2015-195068, filed on Sep. 30, 2015; the entire contents of which are incorporated herein by reference.

FIELD

Embodiments described herein relate generally to a medical image diagnostic apparatus and a medical information display control method.

BACKGROUND

In the field of medicine, medical image diagnostic apparatuses configured to image the inside of a subject with use of radiation such as X-rays, ultrasound waves, nuclear magnetic resonance, or other methods have hitherto been used. For example, a medical image diagnostic apparatus provides a doctor with a medical image in which the inside of a subject is photographed. The doctor views the provided medical image to observe the conditions of the inside of the subject, thereby making a diagnosis.

Image diagnosis using medical images involves setting a region of interest (ROI) on a medical image and making a diagnosis based on an index value in the set region of interest. For example, elastography using an ultrasound diagnostic apparatus involves imaging the stiffness of living tissue and making a diagnosis with use of various index values measured from an ROI within the image. Specifically, mammary tumor diagnosis involves making a diagnosis by using the ratio of the stiffness of a tumor part to the stiffness of a peripheral region as an index. Liver fibrosis diagnosis involves determining the degree of fibrosis by classifying liver fibrosis into several fibrosis stages depending on the stiffness.

Such a diagnosis based on an index value in a region of interest is not limited to the above-mentioned examples, and there are various diagnostic methods. Even when the same index value is used as in the above-mentioned examples, diagnostic standards vary from one diagnosis to another and cannot be determined uniquely. It is therefore not easy to make a diagnosis based on an index value in a region of interest.

BRIEF DESCRIPTION OF THE DRAWINGS

FIG. 2 is a diagram for describing information stored in internal storage circuitry according to the first embodiment;

FIG. 3A to FIG. 3C are diagrams for describing processing of a region setting function according to the first embodiment;

FIG. 5A and FIG. 5B are diagrams for describing processing of the display control function according to the first embodiment;

FIG. 6 is a flowchart illustrating a processing procedure of the ultrasound diagnostic apparatus according to the first embodiment;

FIG. 7 is a diagram for describing information stored in the internal storage circuitry according to a first modification of the first embodiment;

FIG. 8 is a diagram for describing information stored in the internal storage circuitry according to the first modification of the first embodiment;

FIG. 9 is a diagram for describing information stored in the internal storage circuitry according to the first modification of the first embodiment;

DETAILED DESCRIPTION

Medical image diagnostic apparatuses according to embodiments described herein include processing circuitry configured to: calculate an index value in a region of interest of a subject based on tissue property data collected by scanning on the subject; and determine display characteristics of the region of interest based on the index value.

Referring to the accompanying drawings, a medical image diagnostic apparatus, a medical image processing apparatus, and a medical information display control method according to the embodiments are described below. Note that the case where an ultrasound diagnostic apparatus 1 is applied as an example of a medical image diagnostic apparatus is described in the following embodiments, but the embodiments are not limited thereto. Examples of applications of the medical image diagnostic apparatus include, in addition to the ultrasound diagnostic apparatus 1, an X-ray diagnostic apparatus, an X-ray computed tomography (CT) apparatus, a magnetic resonance imaging (MRI) apparatus, a single photon emission computed tomography (SPECT) apparatus, a positron emission tomography (PET) apparatus, a SPECT-CT apparatus combining a SPECT apparatus and an X-ray CT apparatus, a PET-CT apparatus combining a PET apparatus and an X-ray CT apparatus, and a group of these apparatus.

First Embodiment

Figure 1:
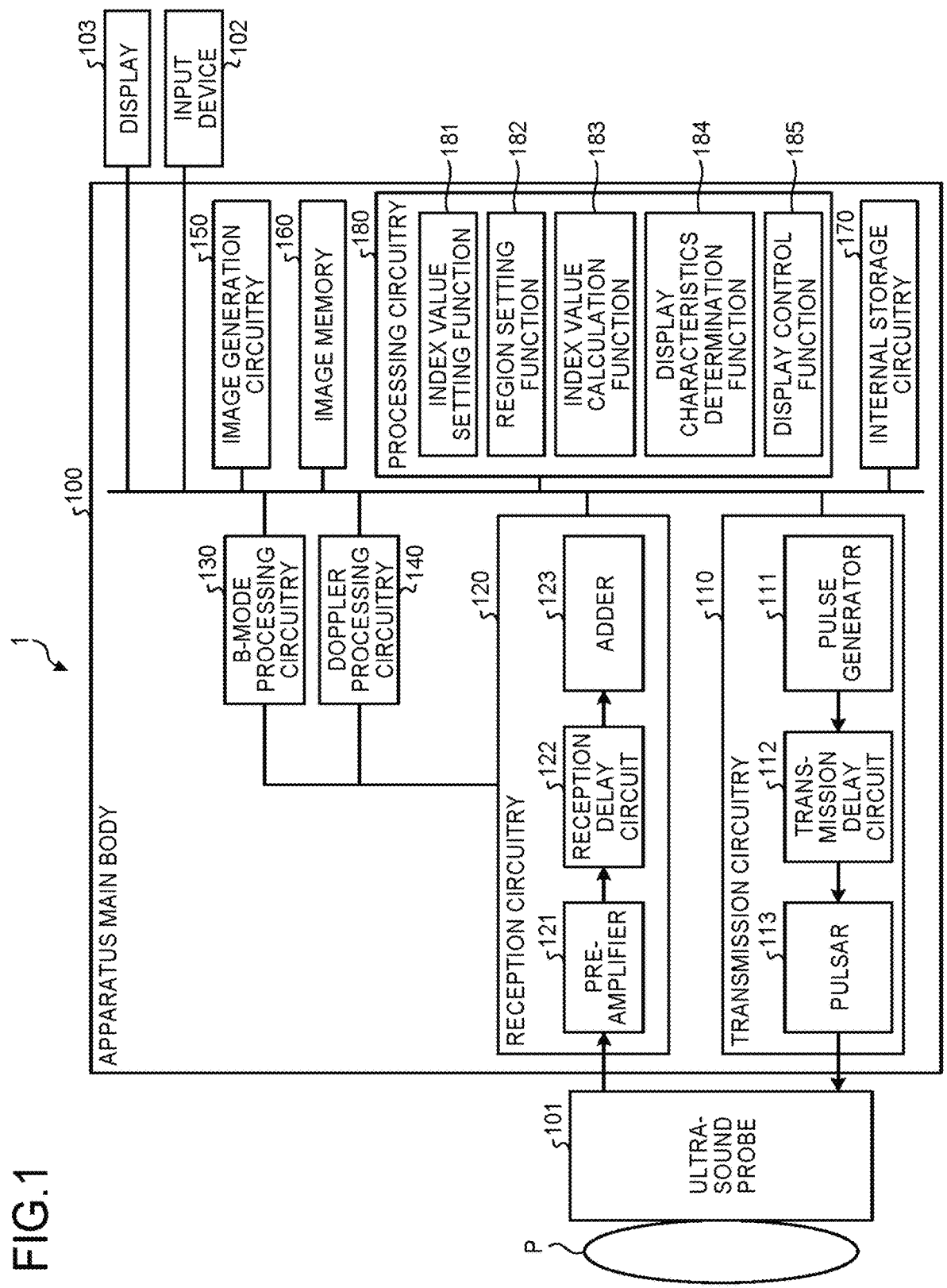
FIG. 1 is a block diagram illustrating a configuration example of an ultrasound diagnostic apparatus according to a first embodiment.

FIG. 1 is a block diagram illustrating a configuration example of an ultrasound diagnostic apparatus 1 according to a first embodiment. As illustrated in FIG. 1, the ultrasound diagnostic apparatus 1 according to the first embodiment includes an apparatus main body 100, an ultrasound probe 101, an input device 102, and a display 103. The ultrasound probe 101, the input device 102, and the display 103 are connected to the apparatus main body 100. Note that a subject P is not included in the configuration of the ultrasound diagnostic apparatus 1.

The ultrasound probe 101 includes a plurality of transducer elements (for example, piezoelectric transducer elements). The transducer elements generate ultrasound waves based on drive signals supplied from transmission circuitry 110 included in the apparatus main body 100 described later. Furthermore, the transducer elements included in the ultrasound probe 101 receive reflected waves from the subject P and convert the reflected waves into electric signals. The ultrasound probe 101 includes a matching layer formed on the transducer elements, a backing member configured to prevent ultrasound waves from propagating backward from the transducer elements, and other components.

When ultrasound waves are transmitted from the ultrasound probe 101 to the subject P, the transmitted ultrasound waves are sequentially reflected by an acoustic impedance discontinuous surface within body tissue of the subject P, and are received by the transducer elements included in the ultrasound probe 101 as reflected wave signals (echo signals). The amplitude of the received reflected wave signal depends on the difference in acoustic impedance at the discontinuous surface by which the ultrasound waves are reflected. Note that, when a transmitted ultrasound pulse is reflected by a moving blood flow or the surface such as the wall of the heart, the resultant reflected wave signal is subjected to frequency shift due to the Doppler effect depending on a velocity component of the moving body in the ultrasound transmission direction.

Note that the first embodiment is applicable to any of the case where the ultrasound probe 101 illustrated in FIG. 1 is a one-dimensional ultrasound probe in which a plurality of piezoelectric transducer elements are arranged in one row, the case where the ultrasound probe 101 is a one-dimensional ultrasound probe in which a plurality of piezoelectric transducer elements are arranged in one row and mechanically oscillated, and the case where the ultrasound probe 101 is a two-dimensional ultrasound probe in which a plurality of piezoelectric transducer elements are two-dimensionally arranged in a grid.

Examples of the input device 102 include a mouse, a keyboard, a button, a panel switch, a touch command screen, a foot switch, a trackball, and a joystick. The input device 102 receives various kinds of setting requests from an operator of the ultrasound diagnostic apparatus 1, and transfers the various kinds of received setting requests to the apparatus main body 100.

The display 103 displays a graphical user interface (GUI) used for the operator of the ultrasound diagnostic apparatus 1 to input various kinds of setting requests with the input device 102, and displays ultrasound image data generated in the apparatus main body 100 and any other data.

The apparatus main body 100 is an apparatus configured to generate ultrasound image data based on reflected wave signals received by the ultrasound probe 101. As illustrated in FIG. 1, the apparatus main body 100 includes the transmission circuitry 110, reception circuitry 120, B-mode processing circuitry 130, Doppler processing circuitry 140, image generation circuitry 150, an image memory 160, internal storage circuitry 170, and processing circuitry 180. The transmission circuitry 110, the reception circuitry 120, the B-mode processing circuitry 130, the Doppler processing circuitry 140, the image generation circuitry 150, the image memory 160, the internal storage circuitry 170, and the processing circuitry 180 are communicably connected to one another.

The transmission circuitry 110 controls transmission directivity in ultrasound transmission. For example, the transmission circuitry 110 includes a pulse generator 111, a transmission delay circuit 112, and a pulsar 113, and supplies drive signals to the ultrasound probe 101. The pulse generator 111 repeatedly generates rate pulses for forming transmission ultrasound waves at a predetermined rate frequency (pulse repetition frequency: PRF). The rate pulse passes through the transmission delay circuit 112 so as to apply a voltage to the pulsar 113 with a different transmission delay time. Specifically, the transmission delay circuit 112 provides each rate pulse generated from the pulse generator 111 with a transmission delay time for each transducer element that is necessary for determining the transmission directivity by focusing the ultrasound waves generated from the ultrasound probe 101 into a beam. The pulsar 113 applies a drive signal (drive pulse) to the ultrasound probe 101 at the timing based on the rate pulse. The transmission direction or the transmission delay time is stored in the internal storage circuitry 170 described later, and the transmission circuitry 110 controls the transmission directivity by referring to the internal storage circuitry 170.

The drive pulse is transmitted from the pulsar 113 to the transducer element included in the ultrasound probe 101 through a cable, and is thereafter converted by the transducer element from the electric signal into a mechanical vibration. The mechanical vibration is transmitted as ultrasound waves inside the living body. The ultrasound waves having transmission delay times different from one transducer element to another are converged to propagate in a predetermined direction. The transmission delay circuit 112 changes a transmission delay time to be provided to each rate pulse, to thereby freely adjust the transmission direction from the transducer element surface. The transmission circuitry 110 provides the transmission directivity by controlling the number and position (transmit aperture) of the transducer elements used for transmission of ultrasound beams and the transmission delay times corresponding to the respective positions of the transducer elements forming the transmit aperture. For example, the transmission delay circuit 112 provides a transmission delay time to each rate pulse generated from the pulse generator 111, to thereby control the position of a focused spot (transmit focus) in the depth direction of ultrasound transmission.

Note that the transmission circuitry 110 has a function of instantaneously changing the transmission frequency, the transmission drive voltage, and other like parameters in order to execute a predetermined scan sequence based on an instruction from the processing circuitry 180 described later. In particular, changes in the transmission drive voltage are achieved by a linear amplifier oscillation circuit capable of instantaneously switching the value of the transmission drive voltage or a mechanism configured to electrically switch a plurality of power supply units.

Reflected waves of the ultrasound waves transmitted from the ultrasound probe 101 reach the transducer elements inside the ultrasound probe 101, and are thereafter converted by the transducer elements from the mechanical vibration into an electric signal (reflected wave signal), to be input to the reception circuitry 120.

The reception circuitry 120 controls reception directivity in ultrasound reception. For example, the reception circuitry 120 includes a preamplifier 121, a reception delay circuit 122, and an adder 123, and performs various kinds of processing on the reflected wave signals received by the ultrasound probe 101 to generate reflected wave data. The preamplifier 121 amplifies the reflected wave signal for each channel, and performs gain correction and analog-to-digital (A/D) conversion. The reception delay circuit 122 provides the A/D-converted reflected wave signal for each channel with a reception delay time necessary for determining the reception directivity. The reception direction or the reception delay time is stored in the internal storage circuitry 170, and the reception circuitry 120 controls the reception directivity by referring to the internal storage circuitry 170. The adder 123 adds the reflected wave signals provided with the reception delay times to generate reflected wave data. This addition processing emphasizes a reflected component of the reflected wave signals from the direction of reception directivity, to thereby form an overall beam for ultrasound transmission and reception. Note that the reception circuitry 120 according to the first embodiment can receive reflected wave signals concurrently and simultaneously.

For example, the B-mode processing circuitry 130 performs logarithmic amplification, envelope detection, and other processing on the reflected wave data received by the reception circuitry 120, to thereby generate data (B-mode data) in which signal intensities at sample points are each represented by the level of luminance. The B-mode data generated by the B-mode processing circuitry 130 is output to the image generation circuitry 150.

For example, the Doppler processing circuitry 140 generates, based on the reflected wave data received by the reception circuitry 120, data (Doppler data) in which motion information on a moving body based on the Doppler effect is extracted at each sample point within a scanning region. Specifically, the Doppler processing circuitry 140 performs frequency analysis on velocity information based on the reflected wave data to extract the blood flow, tissue, and contrast medium echo components derived from the Doppler effect, to thereby generate data (Doppler data) in which moving body information such as the average velocity, dispersion, and power is extracted for multiple points. Examples of the moving body include a blood flow, tissue such as the wall of the heart, and a contrast medium. The motion information (blood flow information) obtained by the Doppler processing circuitry 140 is transmitted to the image generation circuitry 150, and is displayed on the display 103 in color as an average velocity image, a dispersion image, a power image, or an image combining these images.

The image generation circuitry 150 generates ultrasound image data based on data generated by the B-mode processing circuitry 130 and the Doppler processing circuitry 140. The image generation circuitry 150 generates B-mode image data in which the intensities of reflected waves are represented by luminance based on B-mode data generated by the B-mode processing circuitry 130. Furthermore, the image generation circuitry 150 generates Doppler image data indicating moving body information based on Doppler data generated by the Doppler processing circuitry 140. The Doppler image data is velocity image data, dispersion image data, power image data, or image data combining these pieces of data.

In general, the image generation circuitry 150 converts (scan-converts) a scanning line signal column of ultrasound scanning into a scanning line signal column of the video format represented by a television system, to thereby generate display ultrasound image data. Specifically, the image generation circuitry 150 performs coordinate conversion in accordance with the ultrasound scanning mode of the ultrasound probe 101, to thereby generate display ultrasound image data. Furthermore, the image generation circuitry 150 performs various kinds of image processing in addition to scan-conversion, such as image processing (smoothing processing) for regenerating a luminance average value image by using a plurality of image frames after scan-conversion, and image processing (edge enhancement processing) using a differential filter within an image. Furthermore, the image generation circuitry 150 combines the ultrasound image data with supplementary information (such as character information of various parameters, scale marks, and body marks).

In other words, the B-mode data and the Doppler data are ultrasound image data before scan-conversion processing, and the data generated by the image generation circuitry 150 is display ultrasound image data after scan-conversion processing. Note that, when the B-mode processing circuitry 130 generates three-dimensional data (three-dimensional B-mode data and three-dimensional Doppler data), the image generation circuitry 150 performs coordinate conversion in accordance with the ultrasound scanning mode of the ultrasound probe 101, to thereby generate volume data. Then, the image generation circuitry 150 performs various kinds of rendering processing on the volume data to generate display two-dimensional image data.

The image memory 160 is a memory configured to store therein display image data generated by the image generation circuitry 150. Furthermore, the image memory 160 is capable of storing therein data generated by the B-mode processing circuitry 130 and the Doppler processing circuitry 140. The B-mode data and the Doppler data stored in the image memory 160 can be invoked by the operator after diagnosis, for example, and serve as display ultrasound image data via the image generation circuitry 150.

The internal storage circuitry 170 stores therein control programs for executing ultrasound transmission and reception, image processing, and display processing; diagnosis information (for example, patient IDs and doctor's findings); and various kinds of data such as diagnosis protocols and various kinds of body marks. If necessary, the internal storage circuitry 170 is also used to store therein image data stored in the image memory 160. Furthermore, the data stored in the internal storage circuitry 170 can be transferred to an external device via an interface unit (not illustrated).

The processing circuitry 180 controls the overall processing of the ultrasound diagnostic apparatus. Specifically, the processing circuitry 180 controls the processing of the transmission circuitry 110, the reception circuitry 120, the B-mode processing circuitry 130, the Doppler processing circuitry 140, and the image generation circuitry 150 based on various kinds of setting requests input by the operator via the input device 102 and various kinds of control programs and various kinds of data read from the internal storage circuitry 170. Furthermore, the processing circuitry 180 controls the display 103 to display the display ultrasound image data stored in the image memory 160.

Furthermore, the processing circuitry 180 executes an index value setting function 181, a region setting function 182, an index value calculation function 183, a display characteristics determination function 184, and a display control function 185. Respective processing functions to be executed by the index value setting function 181, the region setting function 182, the index value calculation function 183, the display characteristics determination function 184, and the display control function 185, which are the components of the processing circuitry 180, are recorded in the internal storage circuitry 170 in the form of computer programs that can be executed by a computer, for example. The processing circuitry 180 is a processor configured to read each program from the internal storage circuitry 170 and execute the program to implement the function corresponding to the program. Specifically, the index value setting function 181 is a function to be implemented when the processing circuitry 180 reads the program corresponding to the index value setting function 181 from the internal storage circuitry 170 and executes the program. The region setting function 182 is a function to be implemented when the processing circuitry 180 reads the program corresponding to the region setting function 182 from the internal storage circuitry 170 and executes the program. The index value calculation function 183 is a function to be implemented when the processing circuitry 180 reads the program corresponding to the index value calculation function 183 from the internal storage circuitry 170 and executes the program. The display characteristics determination function 184 is a function to be implemented when the processing circuitry 180 reads the program corresponding to the display characteristics determination function 184 from the internal storage circuitry 170 and executes the program. The display control function 185 is a function to be implemented when the processing circuitry 180 reads the program corresponding to the display control function 185 from the internal storage circuitry 170 and executes the program. In other words, the processing circuitry 180 that has read each program has each function illustrated in the processing circuitry 180 in FIG. 1. The respective processing functions executed by the index value setting function 181, the region setting function 182, the index value calculation function 183, the display characteristics determination function 184, and the display control function 185 are described later.

In the above-mentioned embodiment, a description is given of the case where the respective processing functions are implemented by the single processing circuitry 180. However, a processing circuit may be formed by a combination of a plurality of independent processors, and the functions may be implemented by each processor executing a computer program.

The term "processor" used in the above description means, for example, a central processing unit (CPU), a graphics processing unit (GPU), or a circuit such as an application specific integrated circuit (ASIC), a programmable logic device (for example, a simple programmable logic device (SPLD), a complex programmable logic device (CPLD), and a field programmable gate array (FPGA)). The processor implements its functions by reading and executing the programs stored in the storage circuit. Note that a computer program may be directly incorporated in a circuit of the processor instead of storing therein a computer program in the internal storage circuitry 170. In this case, the processor implements its functions by reading and executing the programs incorporated in the circuit. Note that each processor in this embodiment is not limited to the case where each processor is configured as a single circuit, and a plurality of independent circuits may be combined to configure a single processor so as to implement their functions. In addition, the components in FIG. 1 may be integrated into a single processor so as to implement their functions.

The ultrasound diagnostic apparatus 1 according to the first embodiment is an apparatus capable of executing elastography, which measures the stiffness of living tissue and imaging a distribution of the measured stiffness. In elastography, a method of evaluating the stiffness by displacing living tissue is roughly classified into two known methods, i.e., strain imaging and shear wave imaging. Strain imaging is a method of visualizing a relative stiffness based on the size of strain of living tissue at each position within a scanning cross-section, which is observed when the ultrasound probe applies and releases a pressure to and from living tissue from the body surface. Shear wave imaging is a method of applying acoustic radiation force to living tissue from the body surface or applying vibration thereto from an external vibration source to generate a displacement of the living tissue, and observing with time the displacement at each position within a scanning cross-section, thereby determining the propagating velocity of shear waves based on the displacement and determining the elastic modulus.

For example, in the case of executing elastography by shear wave imaging using acoustic radiation force, the ultrasound diagnostic apparatus 1 irradiates a subject P with an ultrasound signal (push pulse) of several hundreds of wavelengths from the ultrasound probe 101, and displaces a part of body tissue of the subject P by the acoustic radiation force. The displaced tissue starts to return to the original position upon the stop of push pulse irradiation, and accordingly, displacement waves, that is, shear waves, propagate in the azimuthal direction. The ultrasound diagnostic apparatus 1 generates shear waves within a scanning cross-section, and repeatedly transmits and receives pulse signals from the ultrasound probe 101 for each position within the scanning cross-section, to thereby collect reflected wave signals including tissue displacement information derived from the propagation of shear waves.

Then, the ultrasound diagnostic apparatus 1 processes the reflected wave signals including the displacement information by the Doppler processing circuitry 140, to thereby extract the tissue displacement caused by the Doppler effect. Then, the ultrasound diagnostic apparatus 1 calculates an arrival time of shear waves based on cross-correlation of temporal changes in the displacement at the respective positions, and determines the propagating velocity of shear waves (hereinafter referred to as "shear wave velocity") based on the calculated arrival time and the distances at the respective positions. The ultrasound diagnostic apparatus 1 allocates a pixel value corresponding to the shear wave velocity to each position within the scanning region, to thereby generate shear wave velocity image data. Note that the value of shear wave velocity corresponds to the stiffness (elastic modulus) of tissue (for example, the tissue becomes stiffer as the shear velocity becomes larger), and hence the shear wave velocity image data is hereinafter referred to also as "stiffness image".

Elastography involves measuring the value of strain or stiffness in a region of interest (ROI) of an obtained stiffness image and making a diagnosis by a doctor based on the measurement value.

For example, in the case of strain imaging, mammary tumor stiffness diagnosis involves determining the ratio of a strain value in an ROI placed within a tumor to a strain value in an ROI placed in peripheral adipose tissue and making a diagnosis that the tumor is malignant when the ratio is equal to or more than a predetermined value (threshold) and that the tumor is benign when the ratio is less than the predetermined value. In the case of shear wave imaging, fibrosis diagnosis of liver that has been diffusely degenerated and the stiffness thereof has changed as a whole involves setting an ROI on a liver stiffness image and determining the fibrosis stage based on the average value of stiffness in the ROI. For example, the index called "Metavir score" classifies the fibrosis stage into five stages of F0, F1, F2, F3, and F4 depending on the progression of fibrosis. In this case, thresholds (cutoff values) for classifying the stages are set in advance, and it is determined which of the stages the calculated average value of stiffness is included, to thereby determine the progress of fibrosis in a non-invasive manner.

In this case, the ROI is set by the operator (examiner), and hence even the same examination result (stiffness image) may vary the measurement results depending on the position or the size of the ROI. This variation partially results from the characteristics of non-uniform body tissue, and also results from artifacts that have been generated because the accurate strain or shear wave velocity has failed to be determined due to cysts containing liquid or blood vessels. In order to reduce the variation resulting from artifacts, a technology of evaluating the value of display of a strain image and controlling the display of the strain image based on the result of evaluation has been proposed. This technology facilitates a determination of strain in a region where estimation accuracy is low, thereby excluding an image containing artifacts from measurement subjects. Furthermore, in order to improve tissue differentiation accuracy and reliability, a technology of generating and displaying a variation image indicating the degree of variation of a stiffness image has been proposed. In this case, a region with a large variation has low reliability, and it is therefore recommended to set an ROI in a region with a small variation.

Evaluation of reliability based on the variation as described above is generally used in shear wave imaging. The variation itself, however, can be a diagnostic index as well. For example, when fibrosis of liver has progressed, a stiff fibrous mass is scattered in soft liver tissue, and the resultant stiffness image is not uniform but looks mottled. Therefore, the degree of variation can be a criterion for determining reliability and be a diagnostic index as well.

As described above, a diagnosis based on an index value (measurement value) in an ROI is not easy. For example, in mammary tumor diagnosis and in liver fibrosis diagnosis, various kinds of thresholds serving as a guide for diagnostic indices have been proposed by research facilities and background diseases, and the threshold may need to be changed depending on situations. Furthermore, in classifying the above-mentioned liver fibrosis stages, it is difficult for the operator to remember all thresholds because the thresholds are necessary for every stage. In addition, in measurement using an ROI, considerations need to be made for both of numerical values of the stiffness index value and the variation index value, which is a burden on the operator. It is therefore desired to facilitate a diagnosis based on an index value in an ROI.

In view of the foregoing, the ultrasound diagnostic apparatus 1 according to the first embodiment facilitates a diagnosis based on an index value in a region of interest by executing each processing function described below. Specifically, the ultrasound diagnostic apparatus 1 calculates, based on data collected by scanning on a subject, an index value in a region of interest of the subject. Then, the ultrasound diagnostic apparatus 1 determines, based on the index value, display characteristics of at least one of the region of interest or numerical information in the region of interest. For example, the ultrasound diagnostic apparatus 1 determines the display color as display characteristics of the region of interest or measurement results in accordance with the index value such as the average value or standard deviation of stiffness (shear wave velocities) in the region of interest, and displays the region of interest or measurement results in the determined display color. Consequently, the ultrasound diagnostic apparatus 1 enables an easy diagnosis to be made based on the index value in the region of interest.

In the following embodiments, a description is given of the case where the shear wave velocity is measured on a stiffness image that is photographed by elastography using shear wave imaging. Specifically, the contents to be described below correspond to processing to be executed when a start instruction to start measuring the shear wave velocity is received from the operator. In this start instruction, "average value of shear wave velocities" is designated as a measurement value, and desired image data is designated as image data to be measured.

Note that the embodiments are not limited to the following description. For example, the processing according to the embodiments is similarly applicable to elastography using strain imaging. The processing according to the embodiments is not limited to elastography and is similarly applicable to measurement on other ultrasound images. The processing according to the embodiments is not limited to the ultrasound diagnostic apparatus and is similarly applicable to other medical image diagnostic apparatuses and other medical image processing apparatuses such as workstation medical image processing apparatuses.

The description returns to FIG. 1. The internal storage circuitry 170 stores therein information on the index value (parameter) for each photographing mode. For example, the internal storage circuitry 170 stores therein an index value table as information on the index value.

FIG. 2 is a diagram for describing information stored in the internal storage circuitry 170 according to the first embodiment. As illustrated in FIG. 2, for example, the internal storage circuitry 170 stores therein, as an index value table for a photographing mode by elastography (elastography mode), information in which the type of index value is associated with a threshold. The type of index value is information indicating the type of index value, and corresponds to, for example, an average value of shear wave velocities or a standard deviation of shear wave velocities. The threshold is a value set for each type of index value, and corresponds to, for example, a value of 2.0 or 1.0. This index value table is registered in advance for each photographing mode by the operator, for example.

As the type of index value, a statistical value of index values of pixels included in an ROI (such as an average value, a median value, a variance, a standard deviation, and an interquartile range) is applicable. As the index value, a value associated with a corresponding pixel or another value that can be calculated from the value is applicable. Specific examples of the index value include, in addition to the shear wave velocity, an average value and a standard deviation of stiffness index values derived from values based on the amounts of displacement or arrival times, and the value of reliability based on the variation in stiffness.

Note that FIG. 2 is only illustrative. For example, in the case where the degree of disease progress is evaluated in several stages, a plurality of thresholds for classifying the stages may be stored for each index value. For example, the index value table may be registered for each examination region (examination purpose) included in patient examination information.

Next, a description is given of respective processing functions of the index value setting function 181, the region setting function 182, the index value calculation function 183, the display characteristics determination function 184, and the display control function 185 executed by the processing circuitry 180.

The index value setting function 181 sets the type of index value and its threshold. For example, the index value setting function 181 refers to the index value table stored in the internal storage circuitry 170 to acquire information on the types of index values from the index value table. Then, the index value setting function 181 displays the acquired information on the types of index values on the display 103 as a candidate list.

In the example illustrated in FIG. 2, the index value setting function 181 displays a candidate list including information such as "average value of shear wave velocities" and "standard deviation of shear wave velocities" as the types of index value. When the operator selects (determines) "standard deviation of shear wave velocities", the index value setting function 181 refers to the index value table to acquire a threshold "1.0" corresponding to the type of index value "standard deviation of shear wave velocities". Then, the index value setting function 181 sets the type of index value "standard deviation of shear wave velocities" and the threshold "1.0".

In this manner, the index value setting function 181 sets the type of index value determined from among the candidates and the threshold corresponding to the determined type of index value.

Note that as described above, "average value of shear wave velocities" is set as a measurement value upon reception of an instruction to start measuring the shear wave velocity. Accordingly, it can be said that the type of index value set by the index value setting function 181 is an index value for determining display characteristics (display characteristics determination index value). Note that a description is given above of the case where "standard deviation of shear wave velocities", which is different from the measurement value, is set as the display characteristics determination index value, but the embodiments are not limited thereto. "Average value of shear wave velocities", which is the measurement value, may be set as the display characteristics determination index value. Furthermore, a plurality of types of index values may be set by the index value setting function 181.

Furthermore, for example, the index value setting function 181 may determine the type of index value and the threshold in accordance with a determined photographing mode. For example, the index value setting function 181 may acquire, in accordance with determined image data to be measured, information on a photographing mode of photographing the image data, and set a suitable type of index value based on the acquired photographing mode information. Specifically, when a stiffness image is determined as a measurement subject, the index value setting function 181 may set a standard deviation of shear wave velocities as the type of index value.

Furthermore, for example, the index value setting function 181 may set the type of index value and the threshold in accordance with an examination region. Specifically, in the case where the index value table is stored for each examination region, the index value setting function 181 may acquire information on the examination region from patient examination information or the like, and set the type of index value and the threshold in accordance with the acquired examination region. Furthermore, for example, the index value setting function 181 may receive an input (manual input) of the type of index value and the threshold from the operator, and set the received type of index value and the received threshold. Furthermore, for example, the index value setting function 181 may set a plurality of thresholds for each index value. This is useful in determining measurement results in several stages, as in the case where the degree of liver fibrosis is diagnosed.

The region setting function 182 sets an ROI for image data to be measured. For example, the region setting function 182 receives an instruction to designate a measurement ROI, which is an ROI indicating the range to be measured, from the operator, and sets the measurement ROI on a stiffness image based on the received instruction.

Figure 3C:
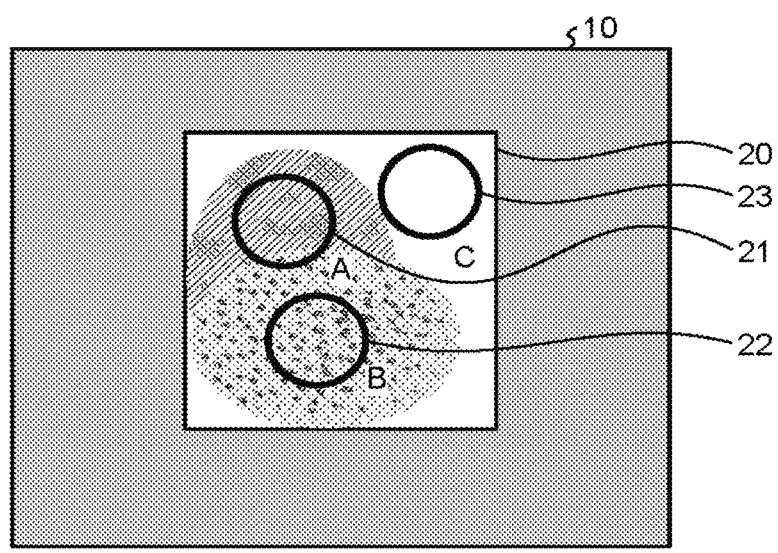

FIG. 3A to FIG. 3C are diagrams for describing processing of the region setting function 182 according to the first embodiment. As illustrated in FIG. 3A, an ultrasound image 10 having a stiffness image 20 superimposed thereon is displayed on the display 103. When the operator inputs an instruction to set a measurement ROI 21, the measurement ROI 21 is displayed on the stiffness image 20. The initial shape, position, and size of the displayed measurement ROI 21 are preset. Then, the operator operates the input device 102 to move the measurement ROI 21 on the stiffness image 20 or change the size of the measurement ROI 21. When the operator changes the shape, position, and size of the measurement ROI 21 to the desired ones in this manner, the region setting function 182 sets the measurement ROI 21 to have the changed shape, position, and size. Furthermore, when a plurality of measurement ROIs are set, a plurality of measurement ROIs 21, 22, and 23 are each arranged on the stiffness image 20 as illustrated in FIG. 3C. Note that, in FIG. 3A to FIG. 3C, symbols A, B, and C indicated near the measurement ROIs 21, 22, and 23 are information (ROI information) for identifying measurement ROIs. For example, the ROI information A, B, and C are displayed on the stiffness image 20 in the state in which given positional relations with the measurement ROIs 21, 22, and 23 are maintained regardless of whether the measurement ROIs 21, 22, and 23 are moved or changed in size.

In this manner, the region setting function 182 sets the measurement ROI(s) on the stiffness image 20. Note that FIG. 3A to FIG. 3C are only illustrative. For example, in the example of FIG. 3C, the case where three measurement ROIs are set is described, but the number of measurement ROIs is not limited to three, and any number of measurement ROIs may be set. Furthermore, the shape of each measurement ROI is not limited to be circular, and any shape such as a rectangle and an ellipse may be applied.

The index value calculation function 183 calculates an index value in an ROI of the subject P based on data collected by scanning on the subject P. For example, the index value calculation function 183 uses information on each pixel included in the measurement ROI set by the region setting function 182 to calculate an index value of the type set by the index value setting function 181.

For example, the index value calculation function 183 acquires, from the internal storage circuitry 170, the value of the shear wave velocity at each pixel included in each of the measurement ROIs 21, 22, and 23. Then, the index value calculation function 183 uses the acquired values of the shear wave velocities to calculate a standard deviation of shear wave velocities for each of the measurement ROIs 21, 22, and 23. Specifically, the index value calculation function 183 calculates a standard deviation "1.01 [m/s]" of shear wave velocities in the measurement ROI 21, a standard deviation "1.35 [m/s]" of shear wave velocities in the measurement ROI 22, and a standard deviation "0.23 [m/s]" of shear wave velocities in the measurement ROI 23.

Subsequently, the index value calculation function 183 determines the rank orders of the calculated standard deviations of shear wave velocities in the measurement ROIs 21, 22, and 23. For example, the index value calculation function 183 compares the standard deviations of shear wave velocities in the measurement ROIs 21, 22, and 23, to thereby determine the rank orders of 1, 2, and 3 in ascending order of standard deviation. In the example of FIG. 3C, the rank order of the measurement ROI 23, which is a uniform region, is determined to be "1", the rank order of the measurement ROI 21, which is a slightly non-uniform region, is determined to be "2", and the rank order of the measurement ROI 22, which is a non-uniform region, is determined to be "3". Note that whether the measurement ROIs are ranked in ascending order or descending order of standard deviation is set in advance for each type of index value, for example. As illustrated in FIG. 3B, when a single measurement ROI 21 is set, the rank order of the measurement ROI 21 is "1".

Furthermore, the index value calculation function 183 calculates a measurement value. For example, the index value calculation function 183 calculates "average value of shear wave velocities" designated by the start instruction as a measurement value. This calculation method is the same as the above-mentioned method of calculating a standard deviation of shear wave velocities, and hence a description thereof is omitted. For example, the index value calculation function 183 calculates an average value "1.84 [m/s]" of shear wave velocities in the measurement ROI 21, an average value "2.09 [m/s]" of shear wave velocities in the measurement ROI 22, and an average value "1.52 [m/s]" of shear wave velocities in the measurement ROI 23.

In this manner, the index value calculation function 183 uses information on each pixel included in each measurement ROT to calculate a display characteristics determination index value and a measurement value for each measurement ROI.

The display characteristics determination function 184 determines display characteristics of at least one of the ROI or the numerical information on the ROI based on the index value. For example, the display characteristics determination function 184 compares the index value calculated by the index value calculation function 183 with the threshold set by the index value setting function 181, to thereby determine the display color as display characteristics.

For example, the display characteristics determination function 184 determines the display colors of the border line of the ROI and the numerical information on the measurement results based on the result of comparison between the index value and the threshold. The relation between the comparison result and the display color is registered in advance in the internal storage circuitry 170. For example, when the standard deviation of shear wave velocities in the measurement ROI is less than the threshold, the display characteristics determination function 184 determines the display color to be "blue", and when the standard deviation of shear wave velocities in the measurement ROI is equal to or more than the threshold, the display characteristics determination function 184 determines the display color to be "red".

Specifically, a description is given of the case where the standard deviations of shear wave velocities in the respective measurement ROIs 21, 22, and 23 are "1.01 [m/s]", "1.35 [m/s]", and "0.23 [m/s]" and the threshold is "1.0". In this case, the display characteristics determination function 184 determines the display colors of the border lines of the measurement ROIs 21 and 22 and the numerals of measurement results to be "red", and determines the display color of the border line of the measurement ROI 23 and the numerals of measurement results to be "blue".

In this manner, the display characteristics determination function 184 compares the index value calculated by the index value calculation function 183 with the threshold set by the index value setting function 181, to thereby determine display characteristics.

Note that the above-mentioned example is only illustrative. For example, a description is given above of the case where the display characteristics of both of the border line of the ROI and the numerical information on the measurement results are determined, but the embodiments are not limited thereto. For example, the display characteristics of any one of the border line of the ROI or the numerical information on the measurement results may be determined. A description is given above of the case where the display color is determined as display characteristics, but the embodiments are not limited thereto. For example, the attributes of lines and characters, such as the thickness, the line type (such as solid line, double line, and dotted line), and the hatching pattern (hatching), may be determined as display characteristics. In other words, any characteristics that can be recognized by the operator when the operator simply views the ROI are applicable as the display characteristics.

Furthermore, a description is given above of the case where the relation between the comparison result and the display color is registered in advance in the internal storage circuitry 170, but the embodiments are not limited thereto. For example, the display color may be set by the operator instead of being set by the index value setting function 181.

The display control function 185 displays at least one of the ROI or the numerical information on the ROI with the display characteristics determined by the display characteristics determination function 184. For example, the display control function 185 displays at least one of the border line of the ROI or the numerical information on the measurement results in the display color determined by the display characteristics determination function 184.

Figure 4A:
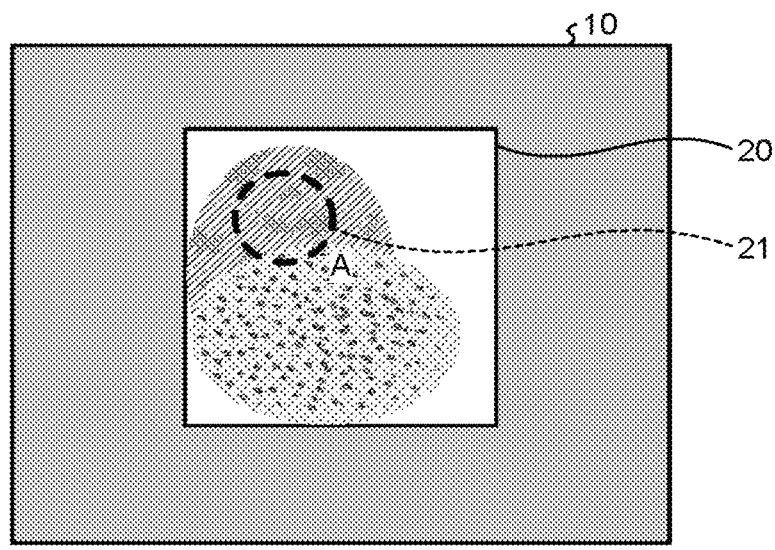
FIG. 4A and FIG. 4B are diagrams for describing processing of a display control function according to the first embodiment.
Figure 4B:
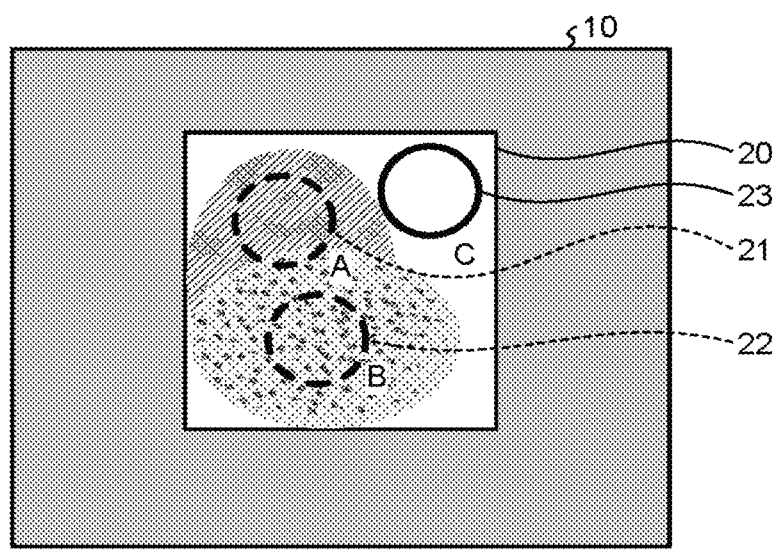

FIG. 4A and FIG. 4B are diagrams for describing processing of the display control function 185 according to the first embodiment. FIG. 4A and FIG. 4B exemplify the case where the border lines of ROIs are displayed with determined display characteristics. In the examples illustrated in FIG. 4A and FIG. 4B, a description is given of the case where the display color of the border line of the measurement ROI 23 is determined to be "blue" and the display colors of the border lines of the measurement ROIs 21 and 22 are determined to be "red". Note that pieces of ROI information on the measurement ROIs 21, 22, and 23 correspond to "A", "B", and "C", respectively. For the sake of illustration, the border line of the ROI displayed in "blue" is illustrated by "solid line" and the border lines of the ROIs displayed in "red" are illustrated by "broken lines".

As illustrated in FIG. 4A, when the measurement ROI 21 is set, the display control function 185 changes the display color of the border line of the measurement ROI 21 set by the region setting function 182 (see FIG. 3B) to "red" determined by the display characteristics determination function 184. As illustrated in FIG. 4B, when the measurement ROIs 22 and 23 in addition to the measurement ROI 21 are set (see FIG. 3C), the display control function 185 changes the display colors of the border lines of the measurement ROIs 22 and 23 set by the region setting function 182 to "red" and "blue" determined by the display characteristics determination function 184, respectively. In this manner, the display control function 185 displays the border lines of the ROIs with the determined display characteristics.

FIG. 5A and FIG. 5B are diagrams for describing processing of the display control function 185 according to the first embodiment. FIG. 5A and FIG. 5B exemplify the case where numerical information on measurement results is displayed with determined display characteristics. In the examples illustrated in FIG. 5A and FIG. 5B, a description is given of the case where numerical information on measurement results for the measurement ROI 23 is determined to be "blue" and numerical information on measurement results for the measurement ROIs 21 and 22 is determined to be "red". Note that FIG. 5A illustrates the measurement results based on the measurement ROI 21 in FIG. 3B, and FIG. 5B illustrates the measurement results based on the measurement ROIs 21, 22, and 23 in FIG. 3C. For the sake of illustration, numerical information displayed in "blue" is illustrated in "white", and numerical information displayed in "red" is illustrated by "hatching".

As illustrated in FIG. 5A, the display control function 185 displays, as measurement results, information in which the rank order, the ROI information, the SWS, and the SD are associated with one another. The rank order indicates the order ranked by the index value calculation function 183. The ROI information is information for identifying an ROI. The SWS indicates an average value of shear wave velocities. The SD indicates a standard deviation of shear wave velocities. When the measurement ROI 21 corresponding to the ROI information "A" is set (see FIG. 3B), the display control function 185 displays numerical information (record) on the measurement results for the ROI information "A" in "red". As illustrated in FIG. 5B, when the measurement ROIs 22 and 23 are also set in addition to the measurement ROI 21 (see FIG. 3C), the display control function 185 displays numerical information on the measurement results for the ROI information "A" and "B" in "red", and displays numerical information on the measurement results for the ROI information "C" in "blue".

In this manner, the display control function 185 displays at least one of the border line of the ROI or the numerical information on the measurement results in the display color determined by the display characteristics determination function 184.

Note that the above-mentioned example is only illustrative. For example, the display control function 185 may display a rank order label for displaying the rank order in the vicinity of each of the measurement ROIs 21, 22, and 23. For example, in FIG. 5B, the measurement results of the measurement ROIs 21, 22, and 23 are displayed in order from the top in accordance with the orders ranked by the index value calculation function 183, but the embodiments are not limited thereto. For example, the measurement results may be displayed in the order by which the measurement ROIs 21, 22, and 23 are set.

Furthermore, for example, both of the border line of the ROI and the numerical information on the measurement results may not be displayed based on display characteristics. For example, any one of the border line of the ROI and the numerical information on the measurement results may be uniformly displayed in a predefined color (such as black).

FIG. 6 is a flowchart illustrating a processing procedure of the ultrasound diagnostic apparatus 1 according to the first embodiment. The processing procedure illustrated in FIG. 6 is started, for example, when a start instruction to start measuring the shear wave velocity is received from the operator.

In Step S101, the processing circuitry 180 determines whether a start instruction to start measuring the shear wave velocity is received. In this start instruction, for example, "average value of shear wave velocities" is designated as a measurement value, and desired image data is designated as image data to be measured. When the start instruction to start measuring the shear wave velocity is received, the processing circuitry 180 starts the processing of Step S102 and subsequent steps. Note that, when the determination in Step S101 is negative, the processing of Step S102 and subsequent steps is not started, and each processing function of the processing circuitry 180 remains in a standby state.

When the determination in Step S101 is positive, in Step S102, the index value setting function 181 sets the type of display characteristics determination index value and the threshold. For example, the index value setting function 181 sets the type of index value determined from among a plurality of candidates and the threshold corresponding to the determined type of index value.

In Step S103, the region setting function 182 sets a measurement ROI. For example, the region setting function 182 receives an instruction to set a measurement ROI 21 from the operator, and sets the measurement ROI 21 having any shape, position, and size designated by the operator.

In Step S104, the index value calculation function 183 calculates a measurement value (shear wave velocity) and a display characteristics determination index value. For example, the index value calculation function 183 calculates "average value of shear wave velocities" designated by the start instruction as a measurement value. Furthermore, the index value calculation function 183 uses information on each pixel included in the measurement ROI set by the region setting function 182 to calculate the index value of the type set by the index value setting function 181.

In Step S105, the index value calculation function 183 determines the rank orders. For example, the index value calculation function 183 compares the standard deviations of shear wave velocities in the measurement ROIs 21, 22, and 23, to thereby determine the rank orders of 1, 2, and 3 in ascending order of standard deviation.

In Step S106, the display characteristics determination function 184 determines display characteristics. For example, the display characteristics determination function 184 compares the index value calculated by the index value calculation function 183 with the threshold set by the index value setting function 181, to thereby determine a display color as the display characteristics.

In Step S107, the display control function 185 changes the display of the measurement ROI. For example, the display control function 185 changes the display color of the border line of the measurement ROI 21 set by the region setting function 182 based on the display characteristics determined by the display characteristics determination function 184.

In Step S108, the display control function 185 displays measurement results. For example, the display control function 185 displays measurement results calculated by the index value calculation function 183 based on the display characteristics determined by the display characteristics determination function 184.

In Step S109, the processing circuitry 180 determines whether another measurement ROI is added. For example, when a measurement ROI is added by the operator, the determination in Step S109 is positive, and the process proceeds to the processing of Step S104. Specifically, the second measurement ROI, the third measurement ROI, . . . are sequentially set. Then, each time a measurement ROI is set, the processing of Step S104 to Step S108 is repeatedly executed to determine display characteristics, and the measurement ROIs and the measurement results are displayed based on the determined display characteristics. On the other hand, when the operator selects not to add a measurement ROI, the determination in Step S109 is negative, and the processing procedure in FIG. 6 is finished.

Note that the example of FIG. 6 is only illustrative. For example, a description is given above of the case where "standard deviation of shear wave velocities", which is different from the measurement value, is set as the display characteristics determination index value, but the embodiments are not limited thereto. "Average value of shear wave velocities", which is the measurement value, may be set as the display characteristics determination index value. In this case, for example, the operator can grasp whether the stiffness of the measurement ROI is larger than a predetermined threshold by simply viewing the color of the border line of the measurement ROI.

Furthermore, for example, both of the processing of Step S107 and the processing of Step S108 are not necessarily required to be executed, and only one of the processing of Step S107 and the processing of Step S108 may be executed. The processing of Step S107 and the processing of Step S108 may be executed in the reverse order.

As described above, in the ultrasound diagnostic apparatus 1 according to the first embodiment, the index value calculation function 183 calculates an index value in an ROI of a subject P based on data collected by scanning on the subject P. Then, the display characteristics determination function 184 determines display characteristics of at least one of the ROI or numerical information on the ROI based on the index value. This configuration of the ultrasound diagnostic apparatus 1 enables an easy diagnosis to be made based on the index value in the region of interest.

For example, the ultrasound diagnostic apparatus 1 according to the first embodiment enables the operator to grasp whether a standard deviation, that is, a dispersion, of shear wave velocities in a measurement ROI is equal to or more than a predetermined threshold by simply viewing the color of the displayed measurement ROI as illustrated in FIG. 4A and FIG. 4B. Consequently, for example, even when no standard value of stiffness is stored for each disease or when no representative value of stiffness or reliability represented by variation or other parameters in the measurement ROI is investigated, the operator can grasp diagnostic indications and reliability of results by simply viewing the colors of the border line of the measurement ROI and the numerical value of the measurement results. In addition, also when a plurality of measurement ROIs are set, the operator can easily grasp which of the reliabilities of measurement results is high or low.

Furthermore, as illustrated in FIG. 5A and FIG. 5B, the ultrasound diagnostic apparatus 1 arranges the measurement results in ascending order of variation, thereby being capable of displaying the measurement results in descending order of reliability. Consequently, for example, even when it is difficult to make a diagnosis based only on information on a single measurement ROI, the operator can make a comparative review of information on another measurement ROI to improve the final diagnostic confidence.

First Modification of First Embodiment

In the first embodiment, a description is given of the case where display characteristics are determined based only on the standard deviation of shear wave velocities, but the embodiments are not limited thereto. For example, the display characteristics may be determined based on a plurality of index values, such as an average value of shear wave velocities and a standard deviation of shear wave velocities. Furthermore, a plurality of thresholds may be set for a single index value. Processing in this case is now described as a first modification of the first embodiment.

FIG. 7 to FIG. 9 are diagrams for describing information stored in the internal storage circuitry 170 according to the first modification of the first embodiment. FIG. 7 exemplifies an index value table for an elastography mode. FIG. 8 exemplifies a display characteristics table storing therein display characteristics based on an average value of shear wave velocities, and FIG. 9 exemplifies a display characteristics table based on a standard deviation of shear wave velocities.

As illustrated in FIG. 7, for example, the internal storage circuitry 170 stores therein, as an index value table for an elastography mode, information in which the type of index value is associated with a threshold. Specifically, the internal storage circuitry 170 stores therein information in which the type of index value "average value of shear wave velocities" is associated with four thresholds "1.4, 1.6, 1.8, and 2.0". Furthermore, the internal storage circuitry 170 stores therein information in which the type of index value "standard deviation of shear wave velocities" is associated with a threshold "1.0".

As illustrated in FIG. 8, for example, the internal storage circuitry 170 stores therein, as a display characteristics table based on an average value of shear wave velocities, information in which the range of the average value of shear wave velocities is associated with a display color. Specifically, in the display characteristics table, a range "2.0 or more" of the average value of shear wave velocities is associated with a display color "black", a range "1.8 to 2.0" of the average value of shear wave velocities is associated with a display color "red", a range "1.6 to 1.8" of the average value of shear wave velocities is associated with a display color "orange", a range "1.4 to 1.6" of the average value of shear wave velocities is associated with a display color "yellow", and a range "less than 1.4" of the average value of shear wave velocities is associated with a display color "white". This display characteristics table indicates that the measurement ROI is displayed in "black" when the average value of shear wave velocities is "2.0 or more", the measurement ROI is displayed in "red" when the average value of shear wave velocities is in the range "1.8 to 2.0", the measurement ROI is displayed in "orange" when the average value of shear wave velocities is in the range "1.6 to 1.8", the measurement ROI is displayed in "yellow" when the average value of shear wave velocities is in the range "1.4 to 1.6", and the measurement ROI is displayed in "white" when the average value of shear wave velocities is "less than 1.4".

As illustrated in FIG. 9, for example, the internal storage circuitry 170 stores therein, as a display characteristics table based on a standard deviation of shear wave velocities, information in which the range of the standard deviation of shear wave velocities is associated with a line type. Specifically, in the display characteristics table, a range "1.0 or more" of the standard deviation of shear wave velocities is associated with a line type "dotted line", and a range "less than 1.0" of the standard deviation of shear wave velocities is associated with a line type "solid line". This display characteristics table indicates that the measurement ROI is displayed by "dotted line" when the standard deviation of shear wave velocities is "1.0 or more", and the measurement ROI is displayed by "solid line" when the standard deviation of shear wave velocities is "less than 1.0".

Figure 10:
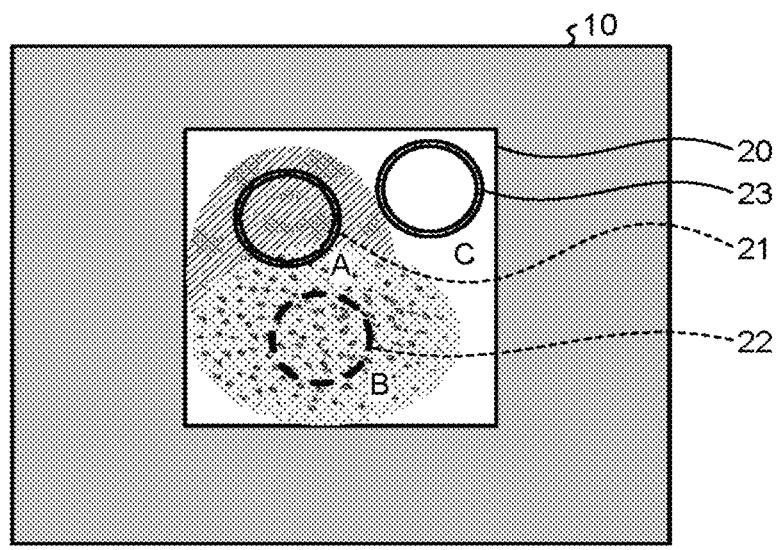
FIG. 10 is a diagram for describing processing of an ultrasound diagnostic apparatus according to the first modification of the first embodiment.

FIG. 10 is a diagram for describing processing of an ultrasound diagnostic apparatus 1 according to the first modification of the first embodiment. FIG. 10 illustrates a display example of measurement ROIs 21, 22, and 23 displayed by the display control function 185 according to the first modification of the first embodiment.

First, in the first modification of the first embodiment, the index value setting function 181 refers to the index value table in FIG. 7 to set "average value of shear wave velocities" and "standard deviation of shear wave velocities" as two types of index value. Here, the index value setting function 181 sets four thresholds "1.4, 1.6, 1.8, and 2.0" for the average value of shear wave velocities, and sets a threshold "1.0" for the standard deviation of shear wave velocities.

Next, the region setting function 182 sets ROIs on image data to be measured. Note that this processing is the same as the above-mentioned processing of the region setting function 182, and hence a description thereof is omitted.

Subsequently, the index value calculation function 183 calculates index values in the ROIs of the subject P based on data collected by scanning on the subject P. Note that this processing is the same as the above-mentioned processing of the index value calculation function 183 except that the index value calculation function 183 calculates "average value of shear wave velocities" and "standard deviation of shear wave velocities" as different types of index value, and hence a description of this processing is omitted.

Then, the display characteristics determination function 184 determines display characteristics of at least one of the ROIs or numerical information on the ROIs based on the index values. A description is now given of the case where the average values of shear wave velocities in the measurement ROIs 21, 22, and 23 are "1.84 [m/s]", "2.09 [m/s]", and "1.52 [m/s]" and the standard deviations of shear wave velocities in the measurement ROIs 21, 22, and 23 are "1.01 [m/s]", "1.35 [m/s]", and "0.23 [m/s]".

In this case, the display characteristics determination function 184 refers to the display characteristics table in FIG. 8 to determine the display color of the border line of each ROI based on the average value of shear wave velocities. Specifically, the average value in the measurement ROI 21 is "1.84 [m/s]", and hence the display characteristics determination function 184 determines the display color of the measurement ROI 21 to be "red". The average value in the measurement ROI 22 is "2.09 [m/s]", and hence the display characteristics determination function 184 determines the display color of the measurement ROI 22 to be "black". The average value of the measurement ROI 23 is "1.52 [m/s]", and hence the display characteristics determination function 184 determines the display color of the measurement ROI 23 to be "yellow".

Furthermore, the display characteristics determination function 184 refers to the display characteristics table in FIG. 9 to determine the line type of the border line of each ROI based on the standard deviation of shear wave velocities. Specifically, the standard deviation in the measurement ROI 21 is "1.01 [m/s]", and hence the display characteristics determination function 184 determines the line type of the measurement ROI 21 to be "dotted line". The standard deviation in the measurement ROI 22 is "1.35 [m/s]", and hence the display characteristics determination function 184 determines the line type of the measurement ROI 22 to be "dotted line". The standard deviation in the measurement ROI 23 is "0.23 [m/s]", and hence the display characteristics determination function 184 determines the line type of the measurement ROI 23 to be "solid line".

In this manner, the display characteristics determination function 184 determines display characteristics of types that differ from one type of index value to another.

Then, the display control function 185 displays the display color and the line type of the border line of each of the measurement ROIs 21, 22, and 23 based on the display characteristics determined by the display characteristics determination function 184. For example, as illustrated in FIG. 10, the display control function 185 changes the border line of the measurement ROI 21 to "red" "dotted line". The display control function 185 changes the border line of the measurement ROI 22 to "black" "dotted line". The display control function 185 changes the border line of the measurement ROI 23 to "yellow" "solid line".

In this manner, in the ultrasound diagnostic apparatus 1 according to the first modification of the first embodiment, the index value calculation function 183 calculates index values of different types. Then, the display characteristics determination function 184 determines display characteristics of types that differ from one type of index value to another. This configuration of the ultrasound diagnostic apparatus 1 enables diagnostic standards based on a plurality of types of index values to be represented on a single image. Consequently, for example, the operator can easily grasp the diagnostic standards based on the types of index values by simply viewing the image.

Second Modification of First Embodiment

For example, an index value of each pixel included in an ROI is not limited to a value that is linked with each pixel, and another value that can be calculated from the value may be applied as the index value. For example, when a stiffness image 20 is generated in elastography, a reliability image corresponding to the stiffness image 20 may be separately generated, and the reliability at the position corresponding to the measurement ROI set on the stiffness image 20 may be calculated as the index value.

Figure 11:
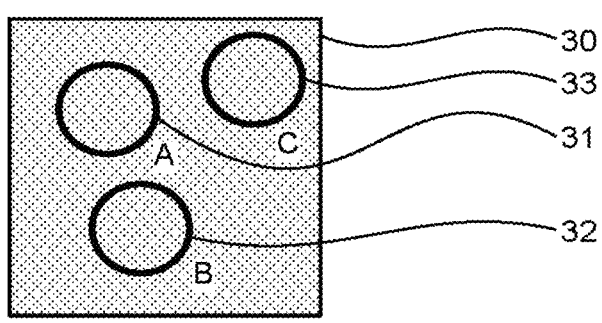
FIG. 11 is a diagram for describing processing of an ultrasound diagnostic apparatus according to a second modification of the first embodiment.

FIG. 11 is a diagram for describing processing of an ultrasound diagnostic apparatus 1 according to a second modification of the first embodiment. FIG. 11 exemplifies a reliability image 30 corresponding to a stiffness image 20. The reliability image 30 is, for example, an image acquired by converting a variance of arrival times of shear waves obtained in the course of generating the stiffness image 20. Specifically, each position on the reliability image 30 is allocated with a pixel value corresponding to a variance of the arrival times within a predetermined range centered around each position on the stiffness image 20.

Referring to FIG. 11, a description is given of the case where the reliability on the reliability image 30 is set as a display characteristics determination index value. As illustrated in FIG. 3C, when the measurement ROIs 21, 22, and 23 are set on the stiffness image 20, the index value calculation function 183 acquires the value of reliability of each pixel included in each of regions 31, 32, and 33 on the corresponding reliability image 30. Then, the index value calculation function 183 uses the acquired reliability values to calculate the reliability of each of the regions 31, 32, and 33. Then, the index value calculation function 183 outputs the calculated reliabilities of the respective regions 31, 32, and 33 as the reliabilities of the respective measurement ROIs 21, 22, and 23.

This configuration of the ultrasound diagnostic apparatus 1 according to the second modification of the first embodiment enables display characteristics to be determined based on the index value of reliability, which is different from the standard deviation (variation) of shear wave velocities. As a result, for example, even when it is difficult to determine the reliability based only on the standard deviation of shear wave velocities, the operator can determine the reliability based on the reliability calculated based on other numerical values. This is useful in diagnosing, for example, a subject tissue in which microstructures having different stiffness are gathered together.

Second Embodiment

In the first embodiment, a description is given of the case where display characteristics of a measurement ROI and its measurement results are determined each time the measurement ROI is set, but the embodiments are not limited thereto. For example, the ultrasound diagnostic apparatus 1 may regard a display region of a stiffness image set on an ultrasound image (B-mode image) as a measurement ROI at the time when the display region is set, and determine display characteristics based on an index value in the measurement ROI. Specifically, the ultrasound diagnostic apparatus 1 executes processing of determining, in accordance with setting of an image ROI indicating the display region of the stiffness image, display characteristics based on an index value in the set image ROI. Consequently, the ultrasound diagnostic apparatus 1 can photograph an image in an image ROI and display the photographed image based on display characteristics without setting any measurement ROI by the operator.

Figure 12:
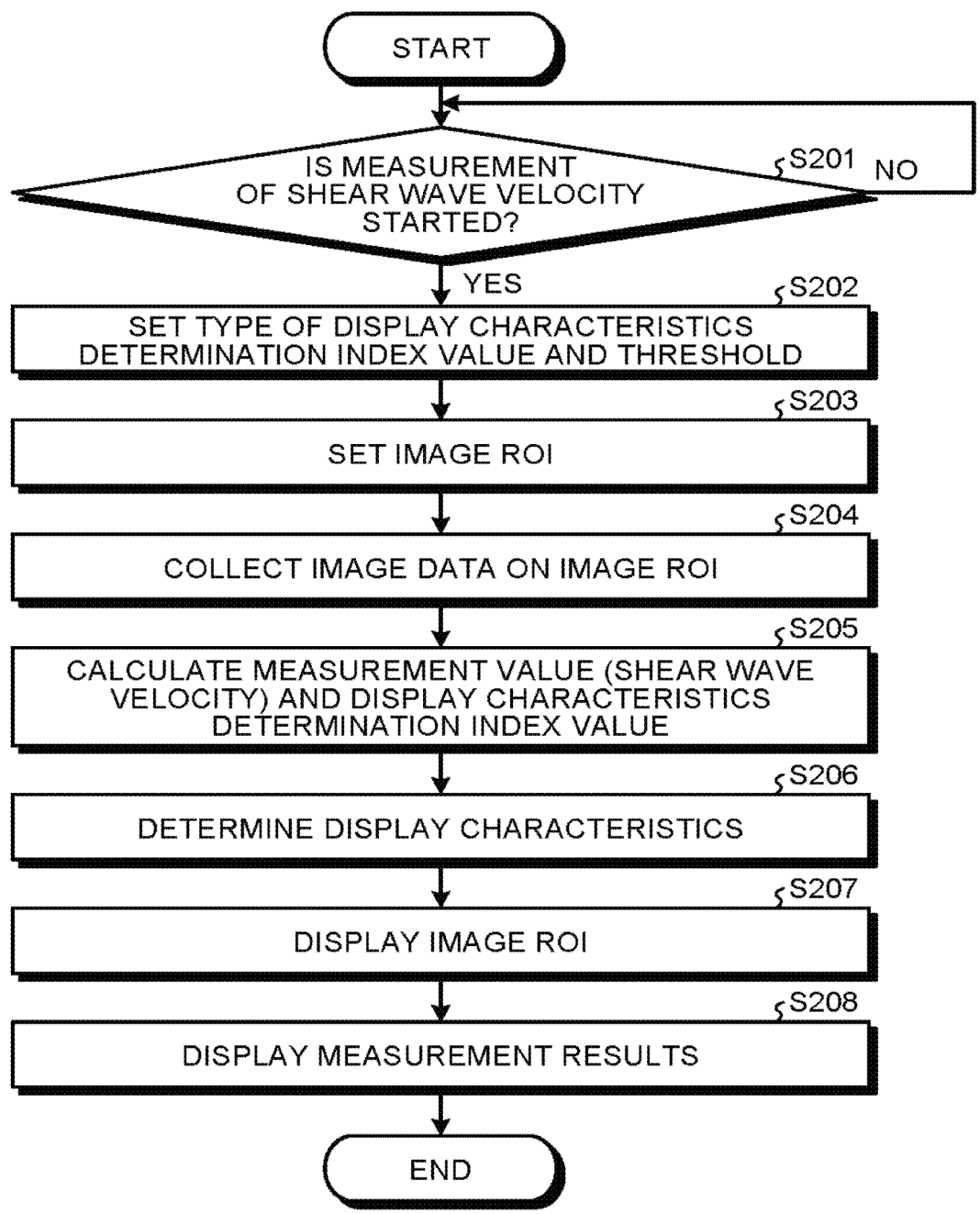
FIG. 12 is a flowchart illustrating a processing procedure of an ultrasound diagnostic apparatus according to a second embodiment.

FIG. 12 is a flowchart illustrating a processing procedure of the ultrasound diagnostic apparatus 1 according to the second embodiment. The processing procedure illustrated in FIG. 12 is started, for example, when a start instruction to start photographing a stiffness image is received from the operator.

In Step S201, the processing circuitry 180 determines whether a start instruction to start photographing a stiffness image is received. In this start instruction, for example, "average value of shear wave velocities" is designated as a measurement value. When the start instruction to start photographing a stiffness image is received, the processing circuitry 180 starts the processing of Step S202 and subsequent steps. Note that, when the determination in Step S201 is negative, the processing of Step S202 and subsequent steps is not started, and each processing function of the processing circuitry 180 remains in a standby state.

When the determination in Step S201 is positive, in Step S202, the index value setting function 181 sets the type of display characteristics determination index value and its threshold. For example, the index value setting function 181 sets the type of index value determined from among a plurality of candidates and the threshold corresponding to the determined type of index value.

In Step S203, the region setting function 182 sets an image ROI. For example, the region setting function 182 receives an instruction to set an image ROI 40 from the operator, and sets the image ROI 40 having any shape, position, and size designated by the operator.

Figure 13:
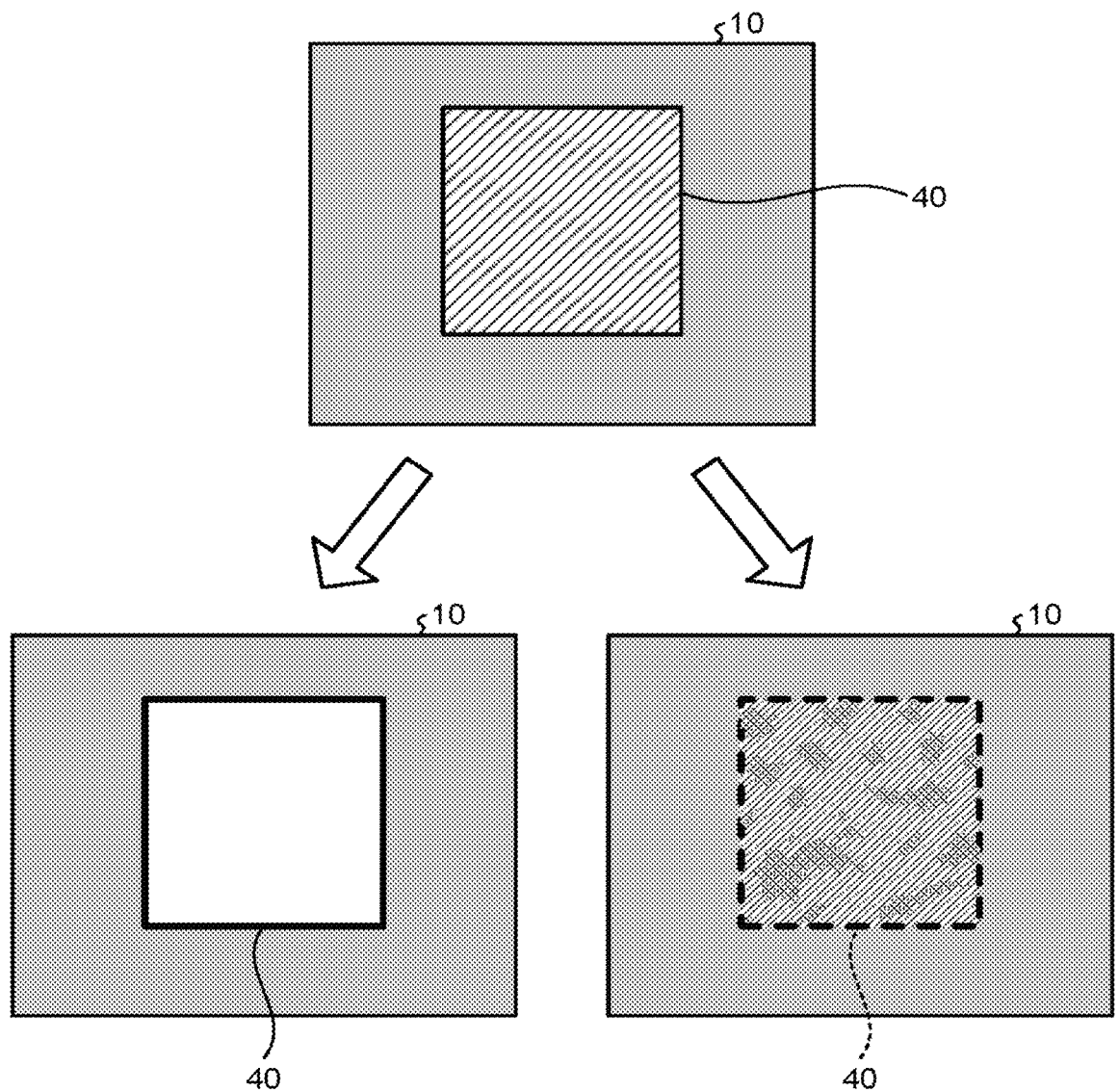
FIG. 13 is a diagram for describing processing of the ultrasound diagnostic apparatus according to the second embodiment.

FIG. 13 is a diagram for describing processing of the ultrasound diagnostic apparatus 1 according to the second embodiment. As illustrated in the upper part of FIG. 13, the region setting function 182 sets an image ROI 40 on an ultrasound image 10. Note that the hatched lines in the image ROI 40 indicate that image data has not been acquired (or is being photographed).

In Step S204, the processing circuitry 180 collects image data on the image ROI 40. For example, the processing circuitry 180 controls the ultrasound probe 101 to transmit a push pulse, and images the image ROI 40 by elastography using shear wave imaging.

In Step S205, the index value calculation function 183 calculates a measurement value (shear wave velocity) and a display characteristics determination index value. For example, the index value calculation function 183 calculates "average value of shear wave velocities" designated by the start instruction as the measurement value. Furthermore, the index value calculation function 183 uses information on each pixel included in a stiffness image corresponding to the image ROI 40 to calculate an index value of the type set by the index value setting function 181.

In Step S206, the display characteristics determination function 184 determines display characteristics. For example, the display characteristics determination function 184 compares the index value calculated by the index value calculation function 183 with the threshold set by the index value setting function 181, to thereby determine the display color as the display characteristics.

In Step S207, the display control function 185 displays the stiffness image corresponding to the image ROI 40. For example, based on the display characteristics determined by the display characteristics determination function 184, the display control function 185 displays the stiffness image corresponding to the image ROI 40 so that the stiffness image is superimposed on the ultrasound image 10.

For example, as illustrated in the lower left part of FIG. 13, when the stiffness image in the image ROI 40 is a uniform tissue cross-section, the display control function 185 displays the border line of the image ROI 40 by the solid line. As illustrated in the lower right part of FIG. 13, on the other hand, when the stiffness image in the image ROI 40 is a slightly non-uniform tissue cross-section, the display control function 185 displays the border line of the image ROI 40 by the broken line.

In Step S208, the display control function 185 displays measurement results. For example, the display control function 185 displays measurement results calculated by the index value calculation function 183 based on the display characteristics determined by the display characteristics determination function 184. Then, the processing circuitry 180 finishes the processing procedure in FIG. 12.

Note that FIG. 12 is only illustrative. For example, the processing of Step S203, which is the processing for setting the image ROI 40, is not necessarily required to be executed. For example, when no image ROI 40 is set, the processing of Step S204 and subsequent steps may be executed on the assumption that the processing procedure is set so that the entire region of the ultrasound image 10 is regarded as the image ROI 40.

In this manner, the ultrasound diagnostic apparatus 1 according to the second embodiment regards the entire stiffness image as a measurement ROI, thereby enabling display characteristics to be determined based on an index value in a photographed image without any time and effort for settings of measurement ROIs by the operator. This configuration enables the operator to easily grasp the diagnostic index and reliability for an obtained entire image by simply viewing the color of the border line of an image ROI and the color of the numerical value of measurement results.

Other Embodiments

In addition to the above-mentioned embodiments, various different embodiments may be implemented.

Combination of the Above-Mentioned Embodiments

For example, the processing described in the first and second embodiments may be implemented in combination.

Figure 14:
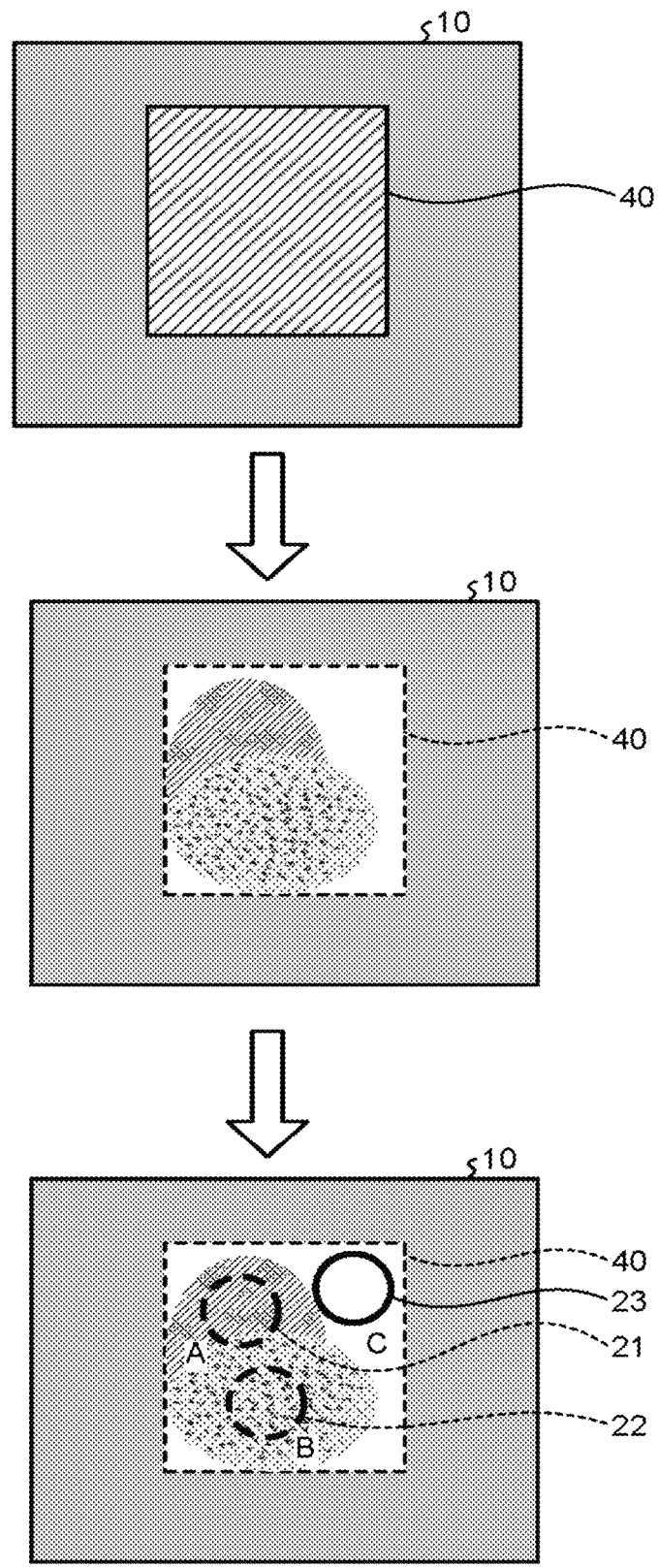
FIG. 14 is a diagram for describing processing of an ultrasound diagnostic apparatus according to another embodiment.

FIG. 14 is a diagram for describing processing of an ultrasound diagnostic apparatus 1 according to other embodiments. As illustrated in the upper part of FIG. 14, the region setting function 182 sets the image ROI 40 on an ultrasound image 10. The hatched lines in the image ROI 40 indicate that image data has not been acquired (or is being photographed).

Subsequently, as illustrated in the middle part of FIG. 14, when image data on a stiffness image corresponding to the image ROI 40 are collected, the index value calculation function 183 calculates an index value (for example, a standard deviation of shear wave velocities) of the stiffness image. Then, the display characteristics determination function 184 determines display characteristics based on the index value calculated by the index value calculation function 183. In the example of the middle part of FIG. 14, the stiffness image in the image ROI 40 includes a uniform tissue cross-section, a slightly non-uniform tissue cross-section, and a non-uniform tissue cross-section. Here, display characteristics of the border line of the image ROI 40 (for example, broken line) are determined depending on the overall index value of the stiffness image. Then, the display control function 185 displays the stiffness image in the image ROI 40, and displays the border line of the image ROI 40 based on the display characteristics determined by the display characteristics determination function 184. Note that this processing corresponds to the processing contents described in the second embodiment.

Then, as illustrated in the lower part of FIG. 14, when measurement ROIs 21, 22, and 23 are individually set on the stiffness image in the image ROI 40, the index value calculation function 183 calculates index values based on information on pixels included in the respective measurement ROIs 21, 22, and 23. Then, the display characteristics determination function 184 determines display characteristics based on the index values calculated by the index value calculation function 183. Here, various values are calculated for the index values of the respective measurement ROIs 21, 22, and 23 depending on whether the background regions thereof are a uniform tissue cross-section, a slightly non-uniform tissue cross-section, or a non-uniform tissue cross-section. Therefore, various display characteristics of the respective measurement ROIs 21, 22, and 23 are determined depending on the calculated index values. Then, the display control function 185 changes the border lines of the respective measurement ROIs 21, 22, and 23 based on the display characteristics determined by the display characteristics determination function 184. Note that this processing corresponds to the processing contents described in the first embodiment.

In this manner, the ultrasound diagnostic apparatus 1 can execute a combination of the processing described in the first and second embodiments.

Applications to Technologies Other than Elastography

For example, the processing according to the above-mentioned embodiments is applicable to technologies other than elastography. For example, the ultrasound diagnostic apparatus 1 is applicable also to luminance analysis of B-mode images. Specific examples of applications of the ultrasound diagnostic apparatus 1 include a contrast-enhanced image luminance analysis function for analyzing a temporal change in luminance in an ROI by using a contrast medium, a statistical analysis function for performing statistical analysis of echo signals in an ROI, and an attenuation analysis function for performing attenuation analysis of echo signals in an ROI.

Application examples of the contrast-enhanced image luminance analysis function include tumor differentiation by mean transit time (MTT). This technology measures a period of time from when a contrast medium reaches a region of interest to when the contrast medium passes by the region of interest as the MTT. Specifically, the MTT is defined as a period of time from when the luminance reaches a given amount relative to the maximum luminance observed when the contrast medium reaches a region of interest to when the luminance decreases to a given amount or less. In general, the MTT is short for a malignant tumor, and the measurement of MTT assists the differentiation. When an ROI for luminance analysis is placed on a luminance analysis screen, the MTT is calculated from a temporal change in luminance in the ROI.

In view of the foregoing, when this embodiment is applied to the contrast-enhanced image luminance analysis function, the MTT can be used as an index value to determine display characteristics. For example, a threshold of the MTT for differentiation is set in advance, and the border line of the ROI can be displayed in red indicating the suspicion of malignancy when the MTT is less than the threshold, and displayed in blue indicating the possibility of benign when the MTT is equal to or more than the threshold.

Examples of applications of the statistical analysis function include the use for diagnosis of the degree of liver fibrosis. For a normal liver, which has a uniform tissue structure, the luminance distribution observed is the same as the one obtained when an ideally uniform scattering substance is observed. When fibrosis has progressed, on the other hand, the tissue structure is non-uniform, and its luminance distribution deviates from the luminance distribution obtained when an ideally uniform scattering substance is observed.

In view of the foregoing, when this embodiment is applied to the statistical analysis function, the luminance distribution in an ROI can be used as an index value to determine display characteristics. For example, when the luminance distribution in the ROI is comparable with the luminance distribution obtained when an ideally uniform scattering substance is observed, the border line of the ROI can be displayed in blue considering the liver as normal, and when the degree of deviation is equal to or more than a given level, the border line of the ROI can be displayed in red suggesting fibrosis.

As described above, the processing according to the above-mentioned embodiments is applicable to the attenuation analysis function and the viscosity analysis function in addition to elastography. In other words, the processing according to the above-mentioned embodiments is suitably applied to tissue property data. Tissue property data includes data generated by elastography, data generated by attenuation analysis, and data generated by viscosity analysis. Specifically, the index value calculation function 183 calculates an index value in a region of interest of a subject based on tissue property data collected by scanning on the subject.

Examples of applications of the attenuation analysis function include the use for determination of fat deposits in the liver. Low fat deposits cause no attenuation in echo signals, but high fat deposits attenuate echo signals. Accordingly, when the amount of attenuation of a luminance value in an ROI (or in the entire image) is less than a predetermined threshold, the border line of the ROI can be displayed in blue, which determines that fat deposits are low, and when the amount of attenuation is equal to or more than the threshold, the border line of the ROI can be displayed in red, which indicates high fat deposits.

Furthermore, each component of each device is conceptually illustrated based on its function, and is not necessarily required to be physically configured as illustrated. In other words, a specific mode for dispersion and integration of the devices is not limited to the illustrated one, and all or part of the devices can be functionally or physically dispersed and integrated in arbitrary units depending on various kinds of loads, usage conditions, and other parameters. In addition, all or any part of each processing function executed by each device may be implemented by a CPU and a computer program analyzed and executed by the CPU, or implemented as hardware by wired logic.

Furthermore, among the processing contents described in the above-mentioned embodiments, all or part of the processing that is described as being automatically executed can also be manually executed, or all or part of the processing that is described as being manually executed can also be automatically executed by a known method. In addition, the processing procedures, the control procedures, the specific names, and the information including various kinds of data and parameters described herein and illustrated in the accompanying drawings can be arbitrarily changed unless otherwise specified.

Furthermore, the medical information display control method described in the above-mentioned embodiment can be implemented by a computer such as a personal computer or a workstation executing a medical information display control program prepared in advance. The display control program can be distributed via a network such as the Internet. Furthermore, the display control program can be recorded in a computer-readable recording medium, such as a hard disk, a flexible disk (FD), a CD-ROM, an MO, and a DVD, and executed by a computer reading the program from the recording medium.

According to at least one of the embodiments described above, a diagnosis based on an index value in a region of interest can be easily made.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising processing circuitry configured to:
   calculate a plurality of different types of index values in a region of interest (ROI) of a subject in a common imaging mode; and
   determine, for at least one of the ROI or numerical information on the ROI, different types of display characteristics corresponding to the types of the index values based on the calculated index values,
   wherein the different types of display characteristics are display characteristics at an identical position in the ROI or the numerical information in the ROI,
   wherein the processing circuitry determines, as the display characteristics, a display color and at least one of a thickness, a line type, and a hatching pattern of a border line of the ROI and a character of numerical information on the ROI.

2. The medical image diagnostic apparatus according to claim 1, wherein the processing circuitry
   receives an instruction to designate the ROI from an operator, and set the ROI to data collected by the imaging mode.

3. The medical image diagnostic apparatus according to claim 1, wherein the imaging mode is at least one of elastography mode, attenuation analysis mode, and viscosity analysis mode.

4. The medical image diagnostic apparatus according to claim 1, wherein the processing circuitry determines display characteristics of numerical information calculated for the ROI.

5. The medical image diagnostic apparatus according to claim 1, wherein the processing circuitry is further configured to:
   set a type of the index value and a threshold of the index value;
   calculate an index value of the set type; and
   determine the display characteristics based on the calculated index value and the set threshold of the index value.

6. The medical image diagnostic apparatus according to claim 5, wherein the processing circuitry sets at least one of the type of the index value or the threshold through input from an operator.

7. The medical image diagnostic apparatus according to claim 5, wherein the processing circuitry sets the type of the index value determined from among a plurality of candidates and the threshold.

8. The medical image diagnostic apparatus according to claim 5, wherein the processing circuitry sets the type of the index value and the threshold in accordance with the imaging mode.

9. The medical image diagnostic apparatus according to claim 5, wherein the processing circuitry receives a designation of an examination region, and sets the type of the index value and the threshold in accordance with the received examination region.

10. The medical image diagnostic apparatus according to claim 1, wherein the processing circuitry further displays at least one of the ROI or numerical information on the ROI based on the determined display characteristics.

11. The medical image diagnostic apparatus according to claim 10, wherein the processing circuitry further determines a rank order of each calculated index value, and displays the determined rank order.

12. The medical image diagnostic apparatus according to claim 11, wherein the processing circuitry further displays numerical information on the ROI in order of the rank.

13. The medical image diagnostic apparatus according to claim 1, wherein the ROI is a measurement ROI for calculating the index value that is based on information on each pixel included in the ROI.

14. The medical image diagnostic apparatus according to claim 1, wherein the ROI is an imaging ROI for collecting image data included in the ROI.

15. The medical image diagnostic apparatus according to claim 1, wherein the index value is a statistical value based on information on each pixel included in the ROI.

16. The medical image diagnostic apparatus according to claim 1, wherein the index value is at least one of an index of image diagnosis based on an image of the ROI or an index of reliability of an image of the ROI.

17. The medical image diagnostic apparatus according to claim 1, wherein the medical image diagnostic apparatus is an ultrasound diagnostic apparatus configured to collect ultrasound data by scanning on the subject as the tissue property data.

18. The medical image diagnostic apparatus according to claim 1, wherein the imaging mode is elastography mode using shear wave.

19. The medical image diagnostic apparatus according to claim 1, wherein the index values include an average value of shear wave velocities and a standard deviation of shear wave velocities.

20. The medical image diagnostic apparatus according to claim 1, wherein the identical position in the ROI is a position of a border line of the ROI.

21. The medical image diagnostic apparatus according to claim 1, wherein the processing circuitry is configured to:
  connect with a storage for storing a table in which a plurality of ranges of the index values defined by a plurality of thresholds are associated with the display characteristics corresponding to the ranges; and
  determine, by referring to the table, the display characteristics corresponding to the ranges including the calculated index values of the ROI as display characteristics of the ROI.

22. A medical information display control method, comprising:
  calculating a plurality of different types of index values in a region of interest (ROI) of a subject in a common imaging mode; and
  determining, for at least one of the ROI or numerical information on the ROI, different types of display characteristics corresponding to the types of the index values of the ROI based on the calculated index values,
  wherein the different types of display characteristics are display characteristics at an identical position in the ROI or the numerical information in the ROI,
  wherein the processing circuitry determines, as the display characteristics, a display color and at least one of a thickness, a line type, and a hatching pattern of a border line of the ROI and a character of numerical information on the ROI.

* * * * *